ns**

United States Patent [19]
Sailhan et al.

[11] Patent Number: 6,057,472
[45] Date of Patent: May 2, 2000

[54] HIGHLY PURE ALKYL 2-CYANOACRYLATES

[75] Inventors: Valérie Sailhan, Montpellier; Rosy Eloy, Chasse sur Rhône; Louis Giral; François Schué, both of Montpellier, all of France

[73] Assignee: Merck Patent GmbH, Germany

[21] Appl. No.: 09/129,951

[22] Filed: Aug. 6, 1998

[30] Foreign Application Priority Data

Jul. 8, 1997 [EP] European Pat. Off. ............... 97113612

[51] Int. Cl.[7] .................................................. C07C 255/00
[52] U.S. Cl. .............................................................. 558/381
[58] Field of Search ............................................. 558/381

[56] References Cited

FOREIGN PATENT DOCUMENTS 3409716  7/1985  Germany .

*Primary Examiner*—Samuel Barts
*Attorney, Agent, or Firm*—Millen, White, Zelano, & Branigan, P.C.

[57] ABSTRACT

A process for the preparation of a highly pure alkyl 2-cyanoacrylate, wherein alkyl has 1–10 C atoms, characterized in that a) formaldehyde is reacted with an alkyl cyanoacetate ester by means of a catalyst in a solvent mixture selected from the group comprising ethylacetate, diglyme, dichloroethane and benzene, yielding an oligo-(alkyl 2-cyanoacrylate);

b) the product of (a) is separated in the form of a solid;

c) the product of (b) is depolymerized under sulfur dioxide atmosphere free from other polymerization inhibitors to yield an alkyl 2-cyanoacrylate with a purity of 98–100%

4 Claims, No Drawings

HIGHLY PURE ALKYL 2-CYANOACRYLATES

The invention relates to a process for the preparation of a highly pure alkyl 2-cyanoacrylate, wherein alkyl has 1–10 C atoms, characterized in that
a) formaldehyde is reacted with an alkyl cyanoacetate ester by means of a catalyst in a solvent mixture selected from the group comprising ethylacetate, diglyme, dichloroethane and benzene, yielding an oligo-(alkyl 2-cyanoacrylate);
b) the product of (a) is separated in the form of a solid;
c) the product of (b) is depolymerized under sulfur dioxide atmosphere free from other polymerization inhibitors to yield an alkyl 2-cyanoacrylate with a purity of 98–100%.

In 1951, cyanoacrylates were showed to possess good adhesive properties. The methyl cyanoacrylate was the first cyanoacrylate commercialized as adhesive in 1958, by the name of Eastman 910. Other cycanoacrylates broke through, such as Super glue, Krazy glue or Histoacryl Blue (butyl 2-cyanoacrylate).

Processes for the preparation of alkyl cyanoacrylates are known. A process by depolymerization of poly-α-alkyl cyanoacrylates and subsequent destillation of the monomers by means of special destillation columns is described in DE 36 38 171. A depolymerization of poly-(alkyl cyanoacrylates) in the presence of $P_2O_5$, hydroquinone and other additives like trikresylphosphate is described in DE 34 09 716. Synthesis and degradation of poly-(alkyl α-Cyanoacrylates) is known by F. Leonard et al., J. Appl. Polymer Science, 10 (1966), 259–272. Leonard uses methanol as solvent for reacting formaldehyde with alkyl cyanoacetate esters.

The capability of alkyl cyanoacrylates to adhere firmly to most surfaces has evoked considerable medical interest. In dental surgery cyanoacrylates can be used as glue for alloys or as adhesives as dental cement. Furthermore, they can be used in the case of bone fractures.

Eastman 910 and Histoacryl blue, respectively based on methyl- and n- butyl cyanoacrylate, were used in surgery of the nose, ears, eyes, and skin. The compounds rapidly polymerize when applied on the surface of biological tissue. However, the alkyl cyanoacrylates used for these purposes show some toxicity. This is the reason why nowadays these surgical adhesives are used only to strengthen sutures and in sprays as hemostatic agents.

Histoacryl Blue is a commercialized adhesive. It is not used as a replacement for sutures in surgery anymore, as studies in vitro have pointed out a certain toxicity after the application of this compound. Consequently, surgeons are presently reluctant to use it (M. Forseth and K. O'Grady, The current status of cyanoacrylate and fibrin tissue adhesives, J. of Long-term Effects of Medical Implants, 1992, 2(4), 221–233; F. Leonard, The n-alkyl alphacyanoacrylate tissue adhesives, Annales New York Academy of Sciences, 1985, 203–213; Toxicity of alkyl 2-anoacrylates: I. Periphal nerve, Arch. Surg., 1966, 93, 441–446).

This toxicity seems to be caused by the presence of impurities during the synthesis and preparation of the alkyl cyanoacrylates. Furthermore, impurities initiate polymerization of the obtained monomers and affect their stability. The monomers obtained by processes of the prior art were found to have purities <98%.

The object of the invention was to discover an improved process for the preparation of alkyl cyanoacrylates which are highly pure.

Surprisingly, it has been found that the alkyl cyanoacrylates obtainable by the process according to the invention show a purity higher than 98%, generally the purities are between 99.00 and 100%, in most cases between 99.98 and 100%.

The scheme of synthesis is as follows:

1. oligomerization

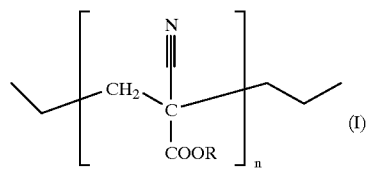

2. depolymerization

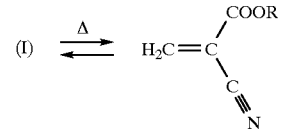

Alkyl cyanoacetates and (para-)formaldehyde are well known compounds. The preparation of alkyl cyanoacetates is carried out analogously to e.g. K. Tarui and S. Morimoto, Japan. 3418(1956); Chem. Abstr. 51, 13910i, by esterification of cyanoacetic acid with the corresponding alcohol.

Suitable solvents used in the first step are, for example, ethylacetate, diglyme, dichloroethane and benzene or mixtures of the solvents. Preferably, ethylacetate, dichloroethane or a mixture of ethylacetate/diglyme or dichloroethane/diglyme is used in the polymerization step.

Suitable catalysts are preferably bases such as piperidine.

The reaction expediently takes place at temperatures between 30 and 120°; it is preferably carried out between 40 and 110°, but particularly preferably between 70 and 110°.

With the oligomers obtained in the form of a solid in the first step, the depolymerization step can be performed without the need of the addition of the anion scavenger $P_2O_5$ or the addition of other radical polymerization inhibitors. The use of $P_2O_5$ and hydroquinone is described by Leonard et al. and in DE 34 09 716.

In contrast to what is known from prior art (DE 34 09 716), there is no necessity to add a free radical stabiliser such as hydroquinone to inhibit free radical polymerization during the depolymerization step.

The depolymerization expediently is carried out under (silicon-)bath temperatures between 100 und 250° C., preferably between 150 and 230° C., but most preferably between 160 and 210°. The depolymerization is carried out at a pressure in the range of 10 Pa to 13 kPa, preferably between 20 Pa and 700 Pa, most preferably between 30 and 400 Pa, but is particularly preferably between 30 and 300 Pa (0.3–3 mbar).

The invention also relates to a process, wherein the polymerization reaction of formaldehyde with alkyl cyanoacetate esters expediently is carried out at temperatures between 10 and 150°, preferably between 20 and 130°, most preferably between 30 and 120° C.

Furthermore, the invention relates to a process, wherein the depolymerization is carried out under temperatures between 100 and 250° C. Additionally, the invention relates to a process, wherein the depolymerization is carried out at a pressure in the range of 10 Pa to 13 kPa.

Alkyl has 1–10 C atoms and preferably is methyl, ethyl, propyl, isopropyl, butyl, tert.-butyl, isobutyl, pentyl (amyl), isopentyl, hexyl, cyclohexyl, heptyl, octyl, nonyl or decyl.

The alkyl 2-cyanoacrylates can be used as adhesives. Preferably, they can be used as surgical glue. Furthermore, they can be used as coatings in pharmaceutical formulations, e.g. for incapsulation of medicaments, as described e.g. by C. Dubernet and J. P. Benoit, L'actualité chimique, 19–28 Décembre (1986).

Moreover, they can be used as resins in microlithography in manufacturing integral circuits.

Hereinbefore and hereinafter, all temperatures are indicated in °C. Determination of purity is determined by gas chromatography (GC) as follows:

|  | condition I | condition II* |
|---|---|---|
| used column | megabore: diameter = 0.536 mm; length = 15 m; stationary phase: DB 225 | megabore: diameter = 0.536 mm; length = 15 m; stationary phase: DB 225 |
| solvent | nitromethane or chloroforme (monomer 10% w/w) |  |
| temperature (column) | 150–170 | 170 (isotherm) |
| temperature (injection) | 220 | 220 |
| temperature (detector) | 250 | 250 |

*the alkyl 2-cyanoacrylate is purely injected

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 196 08 634.5, filed Mar. 6, 1996 is hereby incorporated by reference.

COMPARATIVE EXAMPLE n-hexyl 2-cyanoacrylate and n-butyl 2-cyanoacrylate have been prepared according to Leonard et al. GC analysis under condition I reveals a peak of the solvent as well of the monomer. The analyses confirm the purity values given by Leonard et al. being between 98.5 and 100%.

Hoever, analysing the same compounds under GC condition II, the chromatogram shows additional peaks which were covered by the solvent peak under condition I. Regarding the additional peaks n-hexyl 2-cyanoacrylate exhibits a purity of 96.03% and n-butyl 2-cyanoacrylate shows a value of 97.67%.

EXAMPLE 1

3.48 g (0.11 g mol) of paraformaldehyde and 0.33 ml of piperidine are added to a solution of 12.5 ml of benzene and 12.5 ml of diglyme at about 50°. 19.32 g (0.1157 mol) of n-butyl cyanoacetate is added dropwise at about 90° (reflux condition). After the azeotropic separation of the water the solvents are removed by distillation under reduced pressure (1.33 hPa) without adding phosphorous pentaoxide. The viscous residue is dissolved in warm methanol. After 12 hours at −18° the solid oligo-(n-butyl 2-cyanoacrylate) is separated by filtration and dried.

The depolymerization is carried out in a completely dried apparatus under sulfur dioxide atmosphere (purity of $SO_2$= 99%). The solid oligomer is heated at 170° under reduced pressure [50 Pa (0.5 mbar)]. The monomer n-butyl 2-cyanoacrylate is collected in a cooled receiver; b.p. $80°_{0.5\ mbar}$; purity (GC, condition II) 99.5%.

The following alkyl 2-cyanoacrylates are obtained analogously:

n-hexyl 2-cyanoacrylate, b.p. $90°_{0.5\ mbar}$; purity (GC, condition II) 99.99%;

isobutyl 2-cyanoacrylate, b.p. $65°_{0.5\ mbar}$; purity (GC, condition II) 99.99%;

isoamyl 2-cyanoacrylate, b.p. $73°_{0.5\ mbar}$; purity (GC, condition II) 99.6%;

n-amyl 2-cyanoacrylate, b.p. $70°_{0.5\ mbar}$; purity (GC, condition II) 99.99%;

cyclohexyl 2-cyanoacrylate, b.p. $100°_{0.5\ mbar}$; purity (GC, condition II) 99.99%.

EXAMPLE 2 n-Butyl 2-cyanoacrylate was obtained analogously to Example 1, except that benzene was replaced by ethyl acetate; purity (GC, condition II) 99.99%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for the preparation of a highly pure alkyl 2-cyanoacrylate, wherein alkyl has 1–10 C atoms, characterized in that a) formaldehyde is reacted with an alkyl cyanoacetate ester by means of a catalyst in a solvent selected from the group consisting of ethylacetate, diglyme, dichloroethane, benzene and mixtures thereof, yielding an oligo-(alkyl 2-cyanoacrylate);

b) the product of (a) is separated in the form of a solid;

c) the product of (b) is depolymerized under sulfur dioxide atmosphere free from anion scavenger $P_2O_5$, hydroquinone and other polymerization inhibitors to yield an alkyl 2-cyanoacrylate with a purity of 98–100%.

2. A process according to claim 1, wherein the polymerization reaction of formaldehyde with alkyl cyanoacetate esters is carried out at temperatures between 30 and 120° C.

3. A process according to claim 1, wherein the depolymerization is carried out under temperatures between 100 and 250° C.

4. A process according to claim 1, wherein the depolymerization is carried out at a pressure in the range of 10 Pa to 13 kPa.

* * * * *